US012611138B2

(12) United States Patent
Tainsh

(10) Patent No.: US 12,611,138 B2
(45) Date of Patent: Apr. 28, 2026

(54) SYSTEM FOR MANAGING OCULAR HEALTH

(71) Applicant: Mirth and Sight Limited, Medicine Hat (CA)

(72) Inventor: Josef Tainsh, Medicine Hat (CA)

( * ) Notice: Subject to any disclaimer, the term of this patent is extended or adjusted under 35 U.S.C. 154(b) by 245 days.

(21) Appl. No.: 18/529,070

(22) Filed: Dec. 5, 2023

(65) Prior Publication Data

US 2025/0120646 A1      Apr. 17, 2025

(30) Foreign Application Priority Data

Oct. 12, 2023      (CA) ................................. CA 3216211

(51) Int. Cl.
A61B 5/00          (2006.01)

(52) U.S. Cl.
CPC .......... A61B 5/4809 (2013.01); A61B 5/0075 (2013.01); A61B 5/0077 (2013.01); A61B 5/6802 (2013.01); A61B 5/6891 (2013.01); A61B 5/7405 (2013.01)

(58) Field of Classification Search
CPC ... A61B 5/4809; A61B 5/0075; A61B 5/0077; A61B 5/6802; A61B 5/6891; A61B 5/7405; A61M 21/02; A61M 2021/0044; A61N 5/0618; A61N 5/06; A61F 9/00; A61F 9/04; A61H 5/00
See application file for complete search history.

(56) References Cited

U.S. PATENT DOCUMENTS

| | | | |
|---|---|---|---|
| 5,079,682 A | 1/1992 | Roberts | |
| 10,331,207 B1 * | 6/2019 | Simmons ............. | H04N 13/383 |
| 2010/0205541 A1 * | 8/2010 | Rapaport .............. | G06Q 30/02 |
| | | | 715/753 |
| 2016/0334069 A1 * | 11/2016 | Ji ........................... | F21V 17/02 |
| 2017/0009131 A1 * | 1/2017 | Wataya .................... | F21V 1/17 |
| 2017/0232225 A1 | 8/2017 | Pedersen | |
| 2018/0345034 A1 | 12/2018 | Butzloff | |
| 2020/0397281 A1 * | 12/2020 | Pundlik ................ | A61B 3/0058 |
| 2022/0146854 A1 * | 5/2022 | Simmons .............. | G02B 30/33 |
| 2024/0219990 A1 * | 7/2024 | Dekel ..................... | G06F 1/325 |

FOREIGN PATENT DOCUMENTS

| | | | | |
|---|---|---|---|---|
| CA | 3082936 A1 * | 5/2019 | ........ | G01N 33/6896 |
| GB | 2529278 A | 2/2016 | | |
| WO | 2005079716 A1 | 9/2005 | | |

OTHER PUBLICATIONS

CN 207837557U soldiers of the bed and the vital sign monitoring apparatus, 13 pages. (Year: 2025).*
CN 110716639A the electronic device has a display operation based on eye activity of, 26 pages. (Year: 2025).*

(Continued)

*Primary Examiner* — Tuyen K Vo

(74) *Attorney, Agent, or Firm* — Finch & Maloney PLLC

(57) ABSTRACT

There is provided a system for managing ocular health. At least one light source is controlled by at least one lighting control unit. A localized processing unit controls the light source through communication with the at least one lighting control unit. The localized processing unit is in communication with at least one sensor and uses data streams from the at least one sensor to control the at least one lighting control unit.

14 Claims, 4 Drawing Sheets

(56) References Cited

OTHER PUBLICATIONS

CN 204795242U—Smart phone, 19 pages. (Year: 2025).*

JP H05242972A Illumination Lamp Control System, 8 pages. (Year: 2025).*

G.B.Arden, S.Jyothi, CH Hogg "Regression of early diabetic macular oedema is associated with prevention of dark adaptation" Eye (2011) 25, 1546-1554; doi:10.1038/eye.2011.264, published online Oct. 21, 2011.

"Human eye sensitivity and photometric quantities" https://sites.ecse.rpi.edu/~schubert/Light-Emitting-Diodes-dot-org/Sample-Chapter.pdf.

A Bierman, M G Figueiro, M S Rea (2011), "Measuring and predicting eyelid spectral transmittance" Journal of Biomedical Optics 16(6), 067011 (Jun. 2011).

T.W.Kraft, D.M.Schneeweis, J.L.Schnapf, "Visual Transduction in Human Rod Photoreceptors" Journal of Physiology (1993), 464, pp. 747-765.

E.H. Adelson, "Saturation and Adaptation in the Rod System" Vision Res. vol. 22. pp. 1299 to 1312, available online Mar. 13, 2003.

S.Hestrin and J.I Korenbrot "Activation Kinetics of Retinal Cones and Rods: Response to Intense Flashes of Light", The Journal of Neuroscience, vol. 10 Iss. 6, Jun. 1, 1990.

A.L.Farrar, D.Hill, R.Airey "Home-Use Sleep Mask (Noctura 400) Wear Before and During The COVID-19 Pandemic with its Associated Lockdowns in England." J Opto Ophth. 2022; 3(1):1-14, published Nov. 18, 2022 https://doi.org/10.37191/Mapsci-JOO-3(1)-023.

U.Meyer-Bothling, O.Meyer-Bothling, M.Pinney "A Real-World Single-Centre Study of Patients with Diabetic Macular Oedema Who Wore a Home-Use Sleep Mask (Noctura 400) for One Year" Journal of Ophthalmology, vol. 2021, Article ID 6612126, published Jun. 16, 2021, 13 pages https://noctura.com/wp-content/uploads/2023/07/2.-Meyer-Bothling-et-al-2021.pdf.

* cited by examiner

SYSTEM FOR MANAGING OCULAR HEALTH

FIELD OF THE DISCLOSURE

The present application relates generally to a system for managing ocular health.

BACKGROUND

This section provides background information to facilitate a better understanding of the various aspects of the invention. It should be understood that the statements in this section of this document are to be read in this light, and not as admissions of prior art.

The prevalence of progressive retinopathy based eye disease in modern day society is to some extent inhibited by various existing medical treatments. These can be applied individually or in combination to reduce the rate of onset of retinal degeneration. In certain situations, various treatments can achieve and maintain a relatively good standard of long-term ocular health. However, management of eye care into old age requires careful attention as there are many contributing and convoluting factors. Aside from ocular complications from retinopathy, there are many other associated issues and risks with poor eyesight such as slips, trips, falls and other accidents. These types of accidents can commonly occur in a home-based environment, hospital, sleep-clinic or long-term residence.

At night during sleep, without supplementary light, eyelids are closed, and the retina is in a dark environment. As a result, the eye dark-adapts by activating a large abundance of retinal rods. Rods consume more oxygen than any other cell in the body and the density of rods is much greater than cones throughout most of the retina. A large abundance of active rods results in a significant drop in oxygen levels in the retina, particularly in the inner segment layer. This imbalance in oxygen supply and demand leads to hypoxia, even in regions with no capillary damage. Consequently, dark adaptation of the eye induced hypoxia contributes significantly to diabetic retinopathy progression, primarily due to the heightened activity of rod photoreceptors in darkness.

Diabetic retinopathy is exacerbated by dark adaptation as rod photoreceptors in the retina require increased energy consumption and oxygen than cone photoreceptors. Inhibiting rod photoreceptor activity through nocturnal light therapy may serve to enhance the health of the eyes, and in particular the diabetic retina. This may reduce the need for more invasive treatments like laser therapy or eye injections. Nocturnal light therapy may also help eyes heal after retinopathy damage.

BRIEF SUMMARY

There is provided a system for managing ocular health. At least one light source is controlled by at least one lighting control unit. A localized processing unit controls the light source through communication with the at least one lighting control unit. The localized processing unit is in communication with at least one sensor and uses data streams from the at least one sensor to control the at least one lighting control unit.

In one embodiment, at least one of the at least one light sources is stationary.

In another embodiment, at least one of the at least one light sources is movable.

In one embodiment, the at least one sensor is worn by a user.

In another embodiment, the at least one sensor is positioned on a pillow, bed, or other preferred location. The preferred location may include, but is not limited to, the ceiling, other furniture, and the floor.

In one embodiment, the at least one sensor is a cellular phone.

In one embodiment, the system further includes at least one camera. The at least one camera may be used to determine the location, position, and orientation of a patient's eyelids.

In one embodiment, the at least one lighting control unit causes the at least one light source to dim or turn off when the localized processing unit identifies at least one data stream that indicates that a user is opening their eyes.

In one embodiment, the localized processing unit utilizes machine learning to control the at least one lighting control unit based on the at least one data stream received from the at least one sensor and at least one database of information.

In one embodiment, a non-localized processing unit is provided. The non-localized processing unit is in communication with the localized processing unit such that the at least one data stream is communicable to the non-localized processing unit and at least one updating data stream is communicable to the localized processing unit from the non-localized processing unit.

In one embodiment, the at least one light source emits a light in the spectral range of 360 nm to 830 nm.

In one embodiment, the at least one light source emits a brightness of 100 to 1000 lux.

In one embodiment, an alarm is provided. The alarm provides a signal to awake a user and is controlled by the localized processing unit.

In one embodiment, at least one camera detects an obstruction that prevents light from reaching the patient's eyelids.

BRIEF DESCRIPTION OF THE DRAWINGS

These and other features will become more apparent from the following description in which references are made to the following drawings, in which numerical references denote like parts. The drawings are for the purpose of illustration only and are not intended to in any way limit the scope of the invention to the particular embodiments shown.

DETAILED DESCRIPTION OF THE PREFERRED EMBODIMENTS

Figure 1:
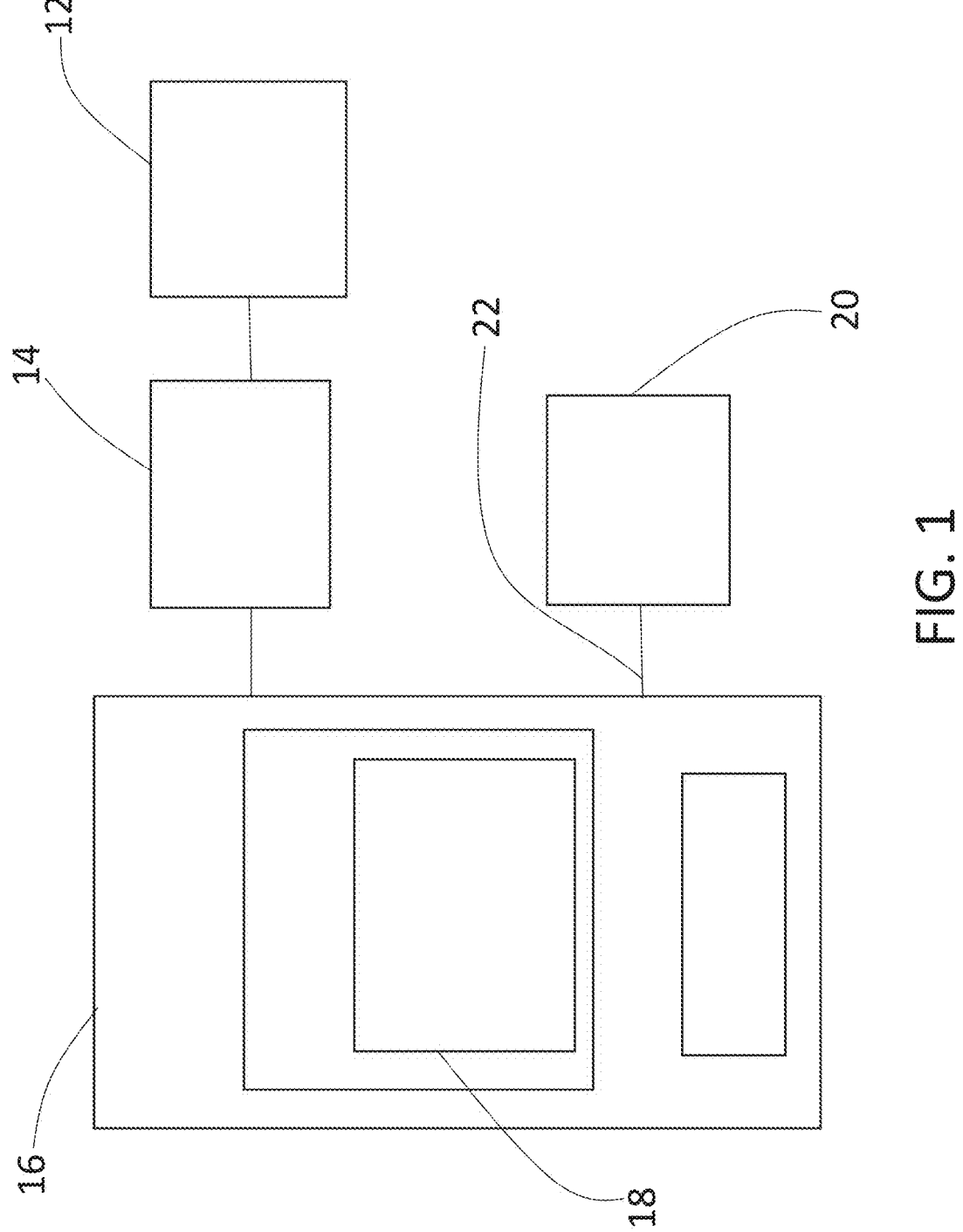
FIG. 1 is a schematic view of the system for managing ocular health.

A system for managing ocular health, generally identified by reference numeral 10, will now be described with reference to FIG. 1 through FIG. 4.

Referring to FIG. 1, a system 10 is provided for assisting in the management of ocular health. System 10 is designed to provide nocturnal light therapy to users. System 10 utilizes at least one light source 12 to shine a light at the user while they sleep to help limit or prevent dark adaptation of the eye by providing illumination to cone photoreceptors in the eye. Light sources 12 preferably emit light in the spectral range of 360 nm to 830 nm and at a brightness of 100 to 1000 lux. A light brightness of 100 to 1000 lux generally results in a brightness of greater than 1 lux reaching the retina as the eyelid blocks a significant amount of light from entering the eye when closed. While having a brightness of 1 lux or greater reaching the retina is preferred, it will be understood that doses of less than 1 lux may promote ocular health and still be beneficial when compared to near complete darkness. It will be understood by a person skilled in the art that different light spectral ranges and brightness may also be used. It may be possible for a user or an operator, such as a doctor or other health professional, to choose a desired color of light by choosing a preferred light wavelength. Individuals have different light color preferences and having the ability to choose the color of light can improve comfort levels during the use of system 10. Lighting control units 14 in communication with light sources 12 are used to control power to light sources 12, light wavelength emitted from light sources 12, light brightness, size of light beams, shape of light beams, specific focus of light beams, and light beam patterns. A single lighting control unit 14 may be used to control multiple light sources 12, a light control unit 14 may be provided for each individual light source 12, or multiple lighting control units 14 may be used to control a single light source 12.

Lighting control units 14 may be manually controlled by a user or their care team, or lighting control units 14 may be automated or semi-automated by a localized processing unit 16. It will be understood by a person skilled in the art that localized processing unit 16 is not required to be physically in the same location as lighting control units 14 and/or light sources 12. The only requirement of localized processing unit 16 is that it be in communication with lighting control units 14. Localized processing unit 16 may be cloud based, located remote relative to lighting control units 14 and light sources 12, or located at the same location as lighting control units 14 and light sources 12. Localized processing unit 16 has a memory device 18 which may be used to store instructions and additional information for system 10. Memory device 18 may be an internal memory, removable memory or combination of internal memory and removable memory. For example, memory device 18 may include instructions or feed backs that cause lighting control unit 14 to turn light sources 12 on at a specific time or in a specific sequence. Instructions may provide limitations to light wavelength and brightness. Instructions may also require the gradual increase or decrease of light wavelength and/or brightness overtime. Instructions may be entered into localized processing unit 16 by a user, a user's care team, or instructions may be a standard setting. It will be understood by a person skilled in the art that different software and algorithms may be employed to achieve desired results of light wavelength, brightness, and treatment time. Localized processing unit 16 may utilize different instructions based on the information available.

Localized processing unit 16 is also in communication with at least one sensor 20 which can provide feedback information about the user or the environment. Sensors 20 may include altimeters, brightness sensors, movement sensors, heart rate sensors, temperature sensors, biometric sensors, cameras, microphones, and any other suitable sensors known to a person skilled in the art. Data streams 22 are sent from sensors 20 to localized processing unit 16 and can affect the instructions or feed backs to lighting control units 14. For example, a heart rate monitor worn by a user may be used to identify when the user is asleep, awake, or uncomfortable. A feedback system may be provided that results in light sources 12 being dimmed when the heart rate is between a certain rate, light sources 12 may be turned on or off when the heart rate reaches a predetermined rate, or light sources 12 may increase brightness or change wavelength of the light at predetermined rates or ranges of heart rate. Different sensors may be used to provide different information to localized processing unit 16. Sensors 20 may be worn by users, positioned around a room such as on pillows, the bed, the ceiling, the floor, or any other preferred location. A cellular phone may act as a sensor through use of the altimeter, microphone, and other features present on many smart phones. Sensors 20 may be provided to provide information about ambient temperature, user temperature, light brightness in specific locations, user positioning, user vitals, and any other useful information known to a person skilled in the art. The more information that is available, the more attuned system 10 may be to a user's needs.

Figure 3:
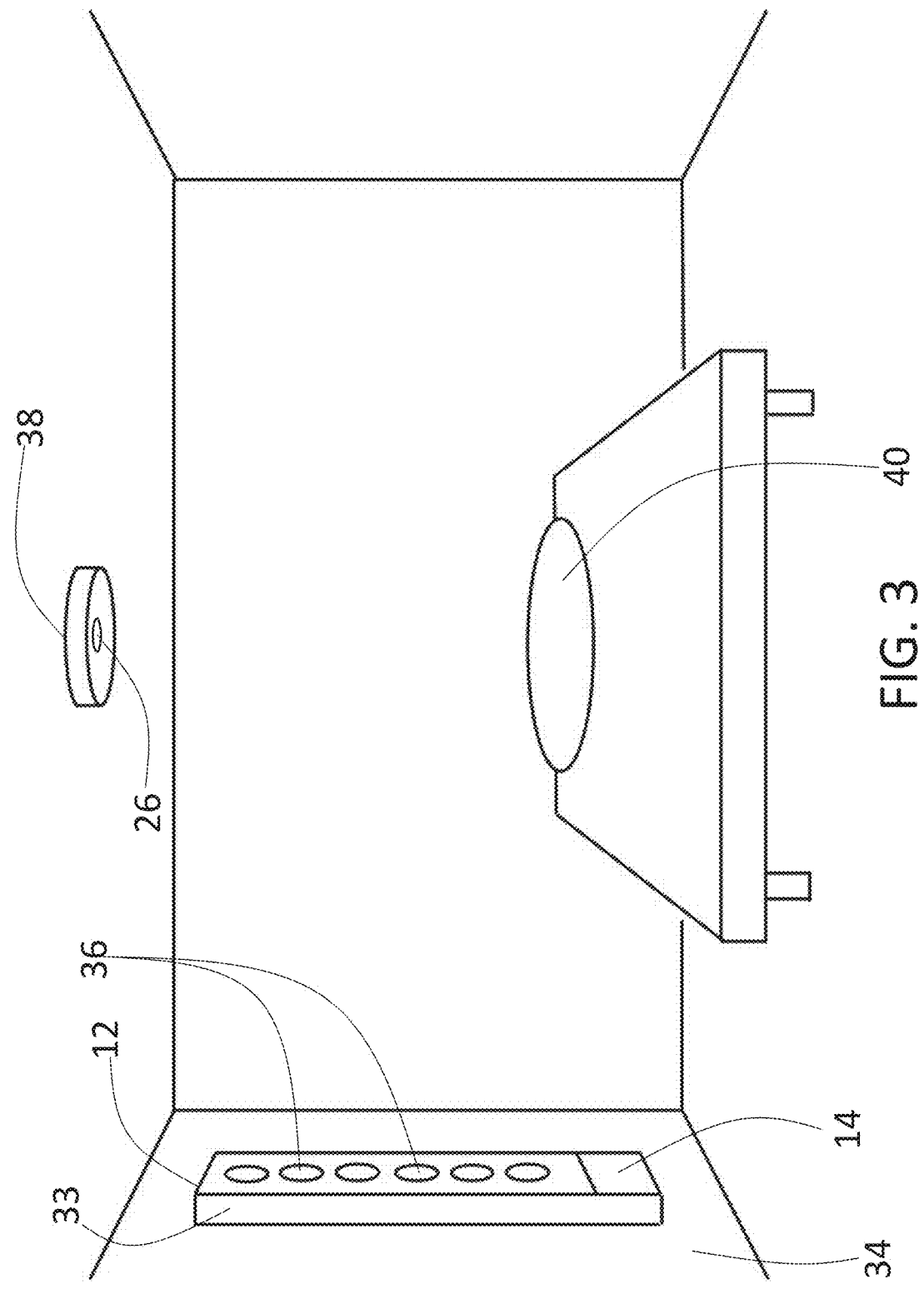
FIG. 3 is a schematic view of the system for managing ocular health in a room for an individual.
Figure 4:
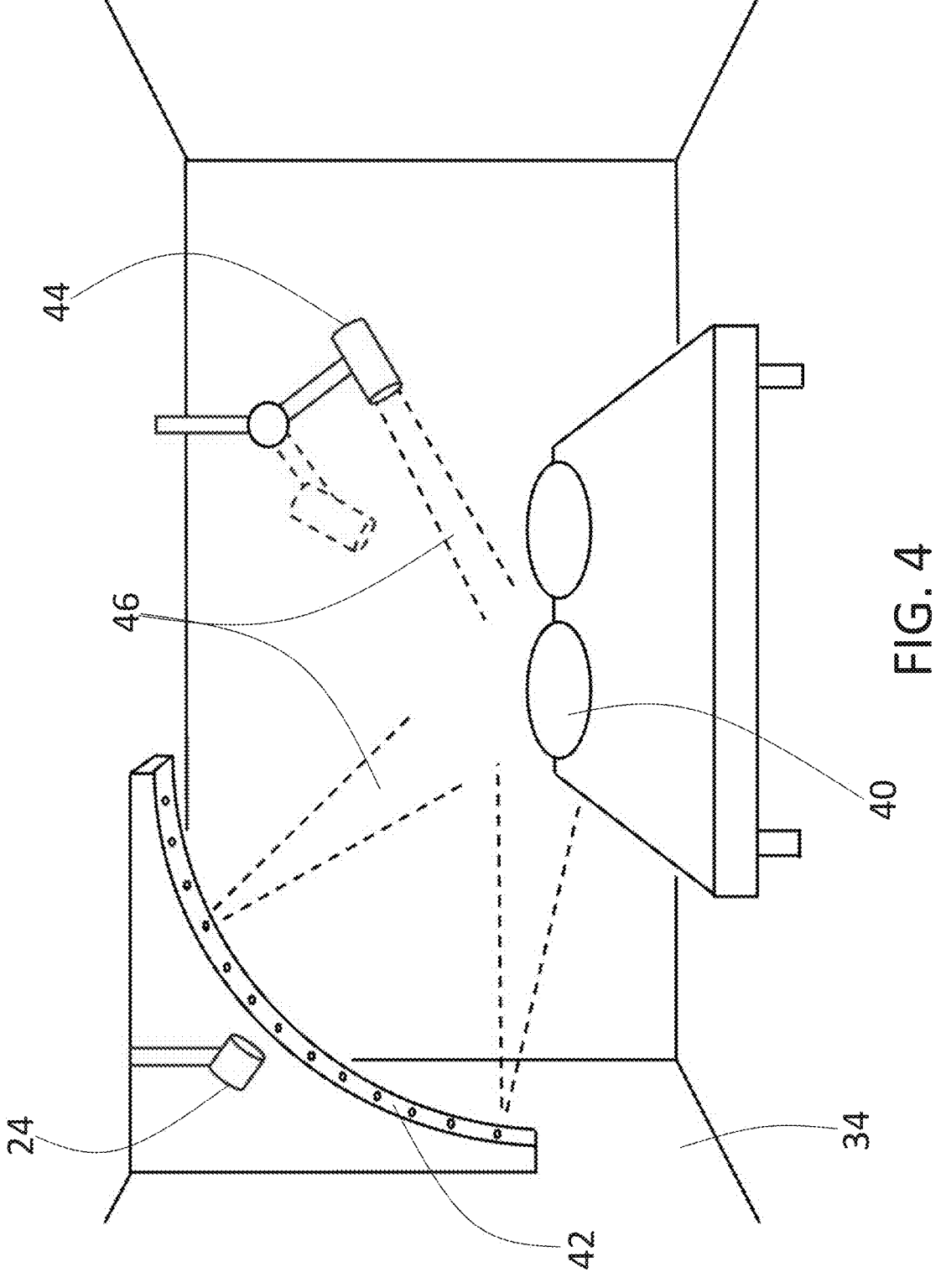
FIG. 4 is a schematic view of the system for managing ocular health in a room for a user and a second individual.

Referring to FIG. 4, at least one camera 24 may be provided to assist in determining the location, position, and orientation of a patient's eyelids. Cameras 24 act as sensors and provide data streams 22 to localized processing unit 16. Cameras 24 may be simple recording devices that relay information to localized processing unit 16 where information is collected or may be smart cameras capable of sending more complex data streams 22 with additional information to localized processing unit 16. Multiple cameras 24 may be placed throughout a room and at different heights to facilitate greater data collection. For example, a camera 24 may be positioned on the ceiling, on a nightstand, on a bed post, on the floor, or in any other suitable location known to a person skilled in the art. Cameras 24 can also provide information about obstructions that block light from reaching a user's eyes. This information may be used to manually or automatically reposition light sources 12 or reposition a user to remove the obstruction. Repositioning of the user may require waking a user. Referring to FIG. 3, an alarm system 26, positioned within a ceiling lamp 38 in the embodiment shown, provides an audio signal to wake a user to allow them to reposition themselves. It will be understood by a person skilled in the art that alarm system may be positioned in any suitable location and may include an audio signal, tactile signal, visual signal, or any other suitable waking signal known to a person skilled in the art. An alarm signal may be provided to an operator to wake a user if needed or the alarm system may alert both the user and an operator to help ensure proper repositioning. Alarm system 26 may be a clock, wearable device, or any other suitable device known to a person skilled in the art.

When the eyes open, sudden exposure to bright light can induce significant retinal glare. This can be an uncomfortable experience and result in blotchy or obscured regions of vision for a time period of up to several minutes. This can create risks for users who must traverse a room shortly after waking. Sensors 20, including cameras 24, may be used to help identify when a user is waking up or opening their eyes. When data suggests that a person is waking, localized processing unit 16 may provide instructions or feedback to dim or turn off light sources. This helps to prevent a glare response in the user's eyes.

To assist with contrast sensitivity, system 10 may be set up to allow a user to fall asleep in a comfortably dark environment. Localized processing unit 16 may control light sources 12 through lighting control units 14 to increase brightness of light sources 12 towards a required dose level over time. A relatively slow and controlled rate can be used to help a user undergoing nocturnal light therapy remain comfortable and consciously unaware of the increased brightness. This process can take upwards of an hour in some cases, although it can be completed more quickly in other cases. This can result in a user's eyes entering a partially dark-adapted state for a period of time. Partial dark-adaptation or dark-adaption may occur when less than 1 lux of incident light reaches the retina. The amount of time in the partial dark-adapted state that may occur during the increased brightness stage is generally only a relative short duration of time when compared to the total time a user will sleep through the night. In more severe cases of retinopathy, the rate of increase in brightness can be quickened to avoid any duration of the user's eyes entering a partially dark-adapted state. System 10 may be set up to balance user comfort versus optimal eye illumination depending upon the severity of the user's retinopathy.

Figure 2:
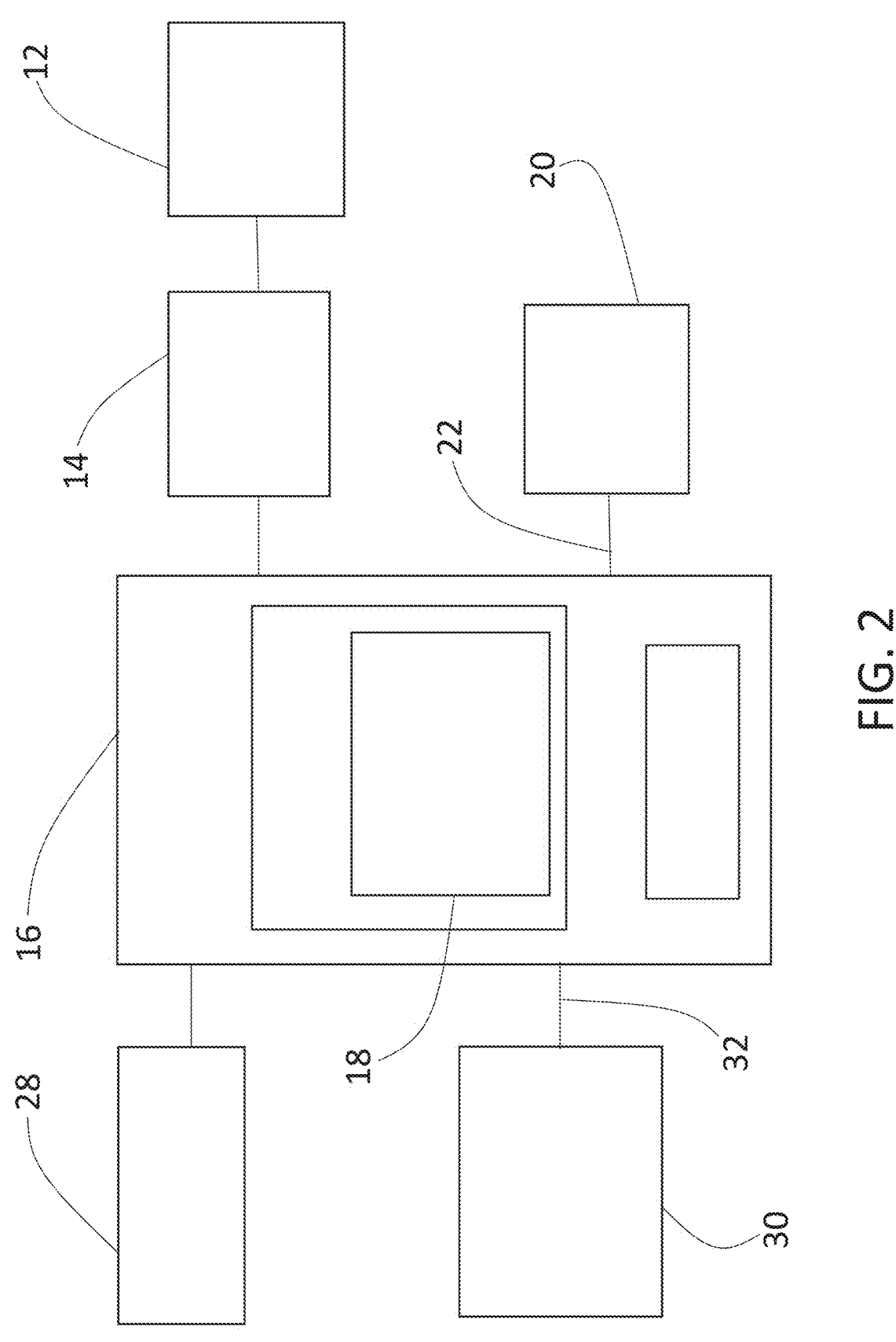
FIG. 2 is a schematic view of the system for managing ocular health with a non-localized processing unit.

Referring to FIG. 2, localized processing unit 16 may be set up with manual controls 28 to allow an operator to manipulate system 10 from a remote or non-remote area. This may be most beneficial in hospitals and sleep studies as it allows an operator to test different settings and user tolerances, however it will be understood by a person skilled in the art that manual controls 28 may be used in any environment. Manual controls 28 may also be used by a user to self-manage system 10 to control comfort trade-offs such as brightness or color. Manual controls 28 may also be useful where light sources 12 are used to control conditions for multiple individuals sleeping in the same area who may have the same or different lighting needs. Manual controls 28 may be available on cellular phones or watches or may require a separate controlling device such as a remote. Manual controls 28 may be useful in collecting and providing additional data for localized processing unit 16 that is useful for individual users such as light color preferences that correlate to specific wavelengths, brightness tolerances, and other information.

Referring to FIG. 2, a non-localized processing unit 30 may be provided that communicates with localized processing unit 16 such that data streams 22 are communicable to non-localized processing unit 30 and at least one updating data stream 32 is communicable to localized processing unit 16 from non-localized processing unit 30. Non-localized processing unit 30 and localized processing unit 16 may be in communication through wireless connections such as wi-fi, Bluetooth or any other suitable wireless connection or may be in communication through wired connections. This allows for updates to software, configuration settings, and remote diagnostics to be performed as needed. Non-localized processing unit 30 has a database that may be used to store back up settings, data, and any other suitable information known to a person skilled in the art. Database stores and maintains information to facilitate data retrieval and processing as required. Non-localized processing unit 30 may communicate with multiple localized processing units 16 used by different users and/or operators. In one embodiment, non-localized processing unit 30 may interact with multiple localized processing units 16 through internet cloud computing. In another embodiment, non-localized processing unit 30 could communicate with multiple localized processing units 16 on a closed computer network architecture that is either wireless or wired. This may be beneficial in hospitals, sleep clinics, or long term care facilities. On a large scale, it is possible for a non-localized processing unit 30 or multiple non-localized processing units 30 to communicate with localized processing units 16 worldwide.

It is possible for non-localized processing unit 30 and localized processing units 16 to have single or multiple users/operators interact with system 10. For example, an eye specialist or doctor may update dose requirements for an individual patient. This information is used to update configuration settings within memory 18 or localized processing unit 16. Analysts may have access to system 10 for research purposes and management/IT may perform maintenance and updates to software and programs. Artificial intelligence with machine learning capabilities may also have access to system 10 through localized processing unit 16 and/or non-localized processing unit 30 to allow for data mining of available data. Artificial intelligence may also be provided with access to system 10 through non-localized processing unit 30 and/or localized processing unit 16 to adapt and update programs and software based on the data available to improve system 10 functionality.

An example of how artificial intelligence and machine learning can work as a part of system 10 is provided. An eye-doctor recognizes that a number of patients have successfully experienced a reduction in the severity of eye disease after using system 10 for a one year time period. The eye-doctor is able to retrieve information from localized processing units 16 used by each patient. Retrieval of information may occur through remote communication with localized processing unit 16 or users may provide information through the use of removable memory storage devices. The eye doctor also obtains data from a similar group of patients who have used light therapy but have not experienced a reduction in severity of retinopathy. The eye doctor may query non-localized processing unit 30 to analyze the data. Artificial intelligence/machine learning may be used to provide a coherent methodology to examine available data and provide feedback as to how different parameters of use of system 10 affect eye health. Artificial intelligence within non-localized processing unit 30 identifies positive correlations in data related to improved lifestyle of various patients as a principal factor with their rate of healing. A software update for system 10 improvements that consider parameters identified by the artificial intelligence as being significant can be made by uploading to localized processing units 16. System updates may be automated by artificial intelligence or may be developed by software developers. Results following system 10 improvements and updates may be monitored by artificial intelligence and/or the eye-doctor to determine if the user experiences improvements.

Artificial intelligence and machine learning may be applied to more quickly recognize the occurrence of similar events through regular use by a single user or similarities between multiple users. For example, real-time data processing of an image obtained from a camera may be used to determine the location, position, and orientation of a user's eyes. Machine learning can be applied to recognize specific facial features at a faster rate or update an overall algorithm that improves facial feature recognition across all patients. This can greatly improve the ability of system 10 to recognize location, position, and orientation of a user's eyes. In addition, different facial features may be indicative of discomfort or of waking and machine learning could correlate data to this effect to allow system to more quickly adapt light sources 12 to a user's needs based on this recognition.

Artificial intelligence may also be useful in providing credible solutions to previously unencountered situations. At the localized processing unit 16 level, artificial intelligence may be used to maximize user comfort, attain higher consistency in user light exposure, and minimize stray light to others sleeping in the same room. For example, a new user begins using system 10 to treat a retinopathy condition as a part of an ocular health management plan they have agreed to with their doctor. After several months with an initial system implementation, the user adds a biometric sensor such as a smart watch so that system 10 can measure the user's heart rate throughout the night. The user's heart rate is correlated by the artificial intelligence as part of a data-mining algorithm that reviews available data. The artificial intelligence recognizes that the user's hear rate drops significantly when system 10 detects or assumes that the user has fallen asleep. As a result, heart rate data is included in future detections of sleep versus wakefulness. In this situation, the artificial intelligence attempts to improve the accuracy of the detection algorithm. System 10 can utilize artificial intelligence to constantly review the accuracy of the detection algorithm against a measure of patent comfort which may be obtained through user insights and/or inputs into system 10. If the user is not satisfied with newly introduced sleeping tolerance arrangements that include heart rate data, the artificial intelligence may reverse previous changes and deduce a different method to incorporate heart rate data that achieves better results for the user. These results may be beneficial for other users and may be utilized by artificial intelligence for future user's implementing heart rate data into their systems 10.

In the embodiment shown in FIG. 3, system 10 is set up for a user who is expected to sleep facing the left side wall 34 of a room. System 10 utilizes a light strip 33 as a light source 12. It will be understood by a person skilled in the art that additional light sources 12 may be positioned throughout the room to improve light coverage if needed. Light strip 33 has a plurality of light bulbs 36 which are controlled by lighting control unit 14. Light bulbs 36 may all be on, all be off, or a combination of light bulbs 36 may be turned on, off, or dimmed by lighting control unit 14. The long dimension of light strip 33 serves to provide a direct line of sight to each closed eyelid for a considerable range of sleeping head positions. A ceiling lamp 38 may be used as a second light source 12 or may provide illumination for navigation throughout the room by providing less bright light when on. When not used as a light source 12, ceiling lamp 38 is likely to provide minimal brightness that would be easily blocked out by eyelids during sleep. Ceiling lamp 38 may be connected to localized processing unit 16 such that localized processing unit 16 controls ceiling lamp 38 regardless of whether it is acting as a light source 12 or not. A user sleeping in this room may wear a smart watch or other wrist worn device. Other sensors may also be included as a part of system 10. Smart watch or wrist worn device may act as both sensor 20 and localized processing unit 16 or a separate localized processing unit 16 such as a smart phone, tablet, or other controller may be used. User may incorporate a luminous pillow 40, luminous clothing, not shown, luminous duvet covers or sheets, not shown, or any other suitable luminous objects to act as light sources 12 or assist in illumination of eyelids. While not shown in the present embodiment, a camera 24 may be included as a part of system 10 and may be used to determine which direction a patient is facing, where their eyes are located, and whether their eyes are opened or closed. If functionality allows, some of light bulbs 36 could be turned off due to redundancy in illuminating the user's closed eyelids. This can serve to reduce stray light and save energy. In situations where there are multiple light sources 12, specific light sources 12 may be turned on and off as needed to maintain specific parameters of lighting.

In the embodiment shown in FIG. 4, system 10 is set up for a user and a second individual. In the present embodiment, the user would sleep on the left side of the bed and the second individual would sleep on the right side of the bed. The second individual does not require use of system 10. It is preferably in this scenario that stray illumination be minimized so as not to disturb the second individual. System 10 utilizes a stationary curved light bar 42 and a movable directing light 44 as light sources 12. A camera 24 is provided to assist in identifying the location and orientation of user's eyes. As can been seen movable directing light 44 may be moved to help maintain light on user as needed. Curved light bar 42 and/or movable directing light 44 may incorporate cameras into them to assist with positioning. Movement of movable directing light 44 may be controlled by localized processing unit 16. Curved light bar 42 has a plurality of light bulbs 36 which may all be on, all be off, or a combination of light bulbs 36 may be turned on, off, or dimmed by lighting control unit 14. In the embodiment shown, light beams 46 are created that cater towards directing light to specific locations to help eliminate stray light and illumination of the second individual. For best results, multiple cameras 24 are provided with the camera line of sight corresponding to each light beam 46 so that cameras 24 have a similar line of sight towards each of the patient's eyes as light beams 46. Light sources 12 with the best line of sight to the patient's eyes can be utilized to illuminate each eyelid. This allows system 10 to track the sleeping position of the patient and actively select the best choice of light source 12 to use. In this configuration, the user can turn their head through a broad range of sleeping positions, from facing the left wall to the ceiling, and even partially turning towards the right wall. However, if the user sleeps facing the right wall, it is unlikely that a direct line of sight to both closed eyelids to a light source 12 would be possible. This is because the second individual in the bed forms an unavoidable optical obstruction and, therefore, there is no requirement to mount light sources to cover this area. In the embodiment shown, only the user's pillow is a luminous pillow 40. It will be understood by a person skilled in the art that luminous pillows are not required but may be useful in ensuring light reaches the user's eyes.

Situations may arise in which only one of a user's eyes requires treatment with system 10. With cameras 24 that can track a user's eyes, it is possible for light beams 46 to be projected such that illumination of a single eyelid is achieved while minimizing stray light from reaching the other eyelid and/or another person sleeping in the bed. Alternatively, different wavelengths and brightness may be beneficial for each eye of a user. This can occur due to different levels of severity in retinopathy or eyelid transmission. It will be understood by a person skilled in the art that other reasons for utilizing different wavelengths and brightness may exist. System 10 may be set up to change the shape, color, and/or brightness of light beams 46 to accommodate different requirements of each eye or different requirements of multiple users within the same room.

Sensors 20 may be used for more than detecting a user's vitals, movements, and more. Sensors 20 may be set up to collect data related to other people in the room who are not actively seeking to use system 10. Movement during sleep may be detected by motion sensors, cameras, or other smart devices that interface with localized processing unit 16. This information may be used to adjust light source 12 wavelength, brightness, beam shape, and any other feature known to a person skilled in the art to improve the comfort of the second person or multiple other people in the room who may become uncomfortable due to light sources 12.

System 10 may require calibration to ensure proper light dosage is received by a user and that stray light is limited where others are in the same room as system 10. There are various mechanisms available to achieve calibration and many will be known to a person skilled in the art. An example of calibration is provided where a user's eyelid transmission, or the amount of light that actually passes through the user's eyelids is already known. In this case, the user's eyelid transmission information may be entered into localized processing unit 16 and a brightness sensor may be positioned on the user's pillow to set the brightness of light sources 12. Localized processing unit 16 receives a data stream 22 from brightness sensor and utilizes data stream to adjust light sources 12 through light controlling units 14 until sufficient lux is obtained at the site of brightness sensor to administer the user's required dose. Brightness sensor is preferably positioned such that it corresponds to the location where user's head generally rests during sleep.

If the user's eyelid transmission has not been predetermined, calibration may start differently to determine eyelid transmission. Software in localized processing unit 16 may be used to walk a user thorough a self-calibration procedure. This may involve the patient lying down as if preparing for sleep and closing their eyes. The user then signals through a controller, remote, or other method, such as a wave to a camera, when they can first see color viewed through their closed eyelids. The system increases light brightness until the user signals that they can identify the specific color through their closed eyelids. To test the calibration, the user may then be asked to signal if they can see an intermittent light cycle as light sources 12 are turned on and off. If the user can confirm that they see the intermittent light cycle, this confirms that a reasonable abundance of light is reaching the retina through the closed eyelids. Finally, the user may be asked to distinguish colors through closed eyelids as this signifies that the retina is out of the scotopic regime and in a partially light-adapted state. Rods are without color and this can be envisaged as the outside surroundings turning dark grey as night sets in. Visual color requires that cones mediate vision. As a result, a confirmation that color can be seen signifies that the patient's retina is at least partially light-adapted.

Where a user wishes to choose a specific colour, or light wavelength, additional calibration may be required since, for example, the eyelid transmittance of green light with a peak wavelength at 540 nm may be measurably different to that of turquoise with a peak of 490 nm. A user's choice of color, therefore, needs to be included or considered as part of the calibration procedure. It will be understood by a person skilled in the art that choice of color may not be an option with all light sources 12 or for the preferred treatment program of all users.

Use of system 10 may be automated or manual. As an example, system 10 may be set up such that it turns on at a specific time, after a sensor or sensors detect specific variables, or by any other mechanism known to a person skilled in the art. In one embodiment, system 10 is operated by a user through activation with localized processing unit 16. Activation may occur through the use of a smart device, such as a cellular phone with app, controller, or any other suitable activating mechanism. As an example only and in relation to FIG. 3, localized processing unit 16 may be activated once user goes to bed. Ceiling lamp 38 is instructed to turn off and light strip 33, or at least one light bulb 34 from light strip 33, is instructed to turn on to a dim setting while the user begins to fall asleep. Sensors 20 such as motion sensors and biometric sensors monitor the user and relay data streams 22 to localized processing unit 16. Once specific parameters of data from sensors that indicate that the user has fallen asleep are received by localized processing unit 16, brightness of light from light strip 33 is slowly increased until a predetermined dose level illuminates the region where the user rests their head during sleep. If data from sensors 20 indicates that the user is waking, for example through increased movement or increased heart rate, brightness of light emitted from light strip 33 may be temporarily reduced to avoid glare situations. A user may be able to communicate with localized processing unit 16 through voice recognition or any other suitable controller as needed to affect light strip 33 brightness, color, or other feature. When the sleep cycle ends and sensors detect that the user is getting out of bed, localized processing unit 16 may instruct ceiling lamp 38 to turn on to a dim setting and light strip 33 to turn off. This can provide some illumination for visual navigation through a room or building while reducing the likelihood of a glare response.

It will be understood by a person skilled in the art that system 10 may be set up in many different orientations to effectively provide nocturnal light therapy to a user. The use of multiple sensors 20 may be used to improve the function of system 10 and artificial intelligence may further improve system 10 through data mining and updates.

Any use herein of any terms describing an interaction between elements is not meant to limit the interaction to direct interaction between the subject elements, and may also include indirect interaction between the elements such as through secondary or intermediary structure unless specifically stated otherwise.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent that changes may be made to the illustrative embodiments, while falling within the scope of the invention. As such, the scope of the following claims should not be limited by the preferred embodiments set forth in the examples and drawings described above, but should be given the broadest interpretation consistent with the description as a whole.

What is claimed is:

1. A system for managing ocular health, comprising:
   at least one light source for shining a light directed at a user's closed eyelids to limit dark adaptation of at least one of a user's eyes by providing illumination to at least one cone photoreceptor in the at least one of the user's eyes;
   at least one lighting control unit, the at least one lighting control unit controlling the at least one light source;
   a localized processing unit having a memory device, the localized processing unit being in communication with the at least one lighting control unit, the localized processing unit controlling the at least one lighting control unit; and
   at least one sensor in communication with the localized processing unit such that at least one data stream from the at least one sensor is sent to the localized processing unit, the localized processing unit utilizing the at least one data stream to control the at least one lighting control unit.

2. The system of claim 1 wherein at least one of the at least one light sources is stationary.

3. The system of claim 1 wherein at least one of the at least one light sources is movable.

4. The system of claim 1 wherein the at least one sensor is worn by a user.

5. The system of claim 1 wherein the at least one sensor is positioned on a pillow, bed, or other preferred location.

6. The system of claim 1 wherein the at least one sensor is a cellular phone.

7. The system of claim 1 further comprising at least one camera, the at least one camera determining the location, position, and orientation of a patient's eyelids.

8. The system of claim 1 wherein the at least one lighting control unit causes the at least one light source to dim or turn off when the localized processing unit identifies at least one data stream that indicates that a user is opening their eyes.

9. The system of claim 1 wherein the localized processing unit utilizes machine learning to control the at least one lighting control unit based on the at least one data stream received from the at least one sensor and at least one database of information.

10. The system of claim 1 further comprising a non-localized processing unit, the non-localized processing unit being in communication with the localized processing unit such that the at least one data stream is communicable to the non-localized processing unit and at least one updating data stream is communicable to the localized processing unit from the non-localized processing unit.

11. The system of claim 1 wherein the at least one light source emits a light in the spectral range of 360 nm to 830 nm.

12. The system of claim 1 wherein the at least one light source emits a brightness of 100 to 1000 lux.

13. The system of claim 1 further comprising an alarm that provides a signal to awake a user in the event that the user needs to reposition, the alarm being controlled by the localized processing unit.

14. The system of claim 7 wherein the at least one camera detects an obstruction that prevents light from reaching the patient's eyelids.

* * * * *